United States Patent [19]

Kasuga et al.

[11] Patent Number: 5,182,398

[45] Date of Patent: Jan. 26, 1993

[54] α-AMINO ACID DIAMIDE AND USE THEREOF AS CUPRIC ION-TRANSPORTING IONOPHORE

[75] Inventors: Kazuyuki Kasuga; Takuji Hirose; Toshikazu Takahashi; Kazuhisa Hiratani, all of Tsukuba, Japan

[73] Assignee: Director-General of Agency of Industrial Science and Technology, Japan

[21] Appl. No.: 840,546

[22] Filed: Feb. 25, 1992

[30] Foreign Application Priority Data

Dec. 17, 1991 [JP] Japan .................................. 3-353342

[51] Int. Cl.⁵ ............................................ C07D 215/38
[52] U.S. Cl. .................................................. 546/171
[58] Field of Search ........................................ 546/171

[56] References Cited

PUBLICATIONS

CA 108(19):167970b A process . . . -methoyquinoline, Bhat, p. 702, 1988.

CA 104(23):207114b Possible . . . -aminoquinolines, Bhat, p. 740, 1986.

Primary Examiner—Mary C. Lee
Assistant Examiner—Joseph K. McKane
Attorney, Agent, or Firm—Lorusso & Loud

[57] ABSTRACT

A diamine derivative expressed by the following general formula (I):

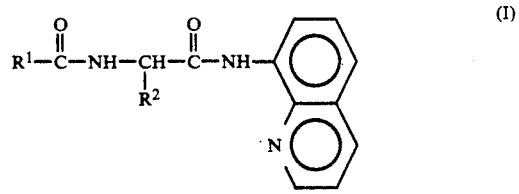

wherein $R^1$ and $R^2$ stand, independently from each other, for a hydrogen atom, an alkyl group, an aralkyl group or an aryl group. The diamide derivative is useful as an ionophore which can selectively transport cupric ions through liquid membranes.

6 Claims, 1 Drawing Sheet

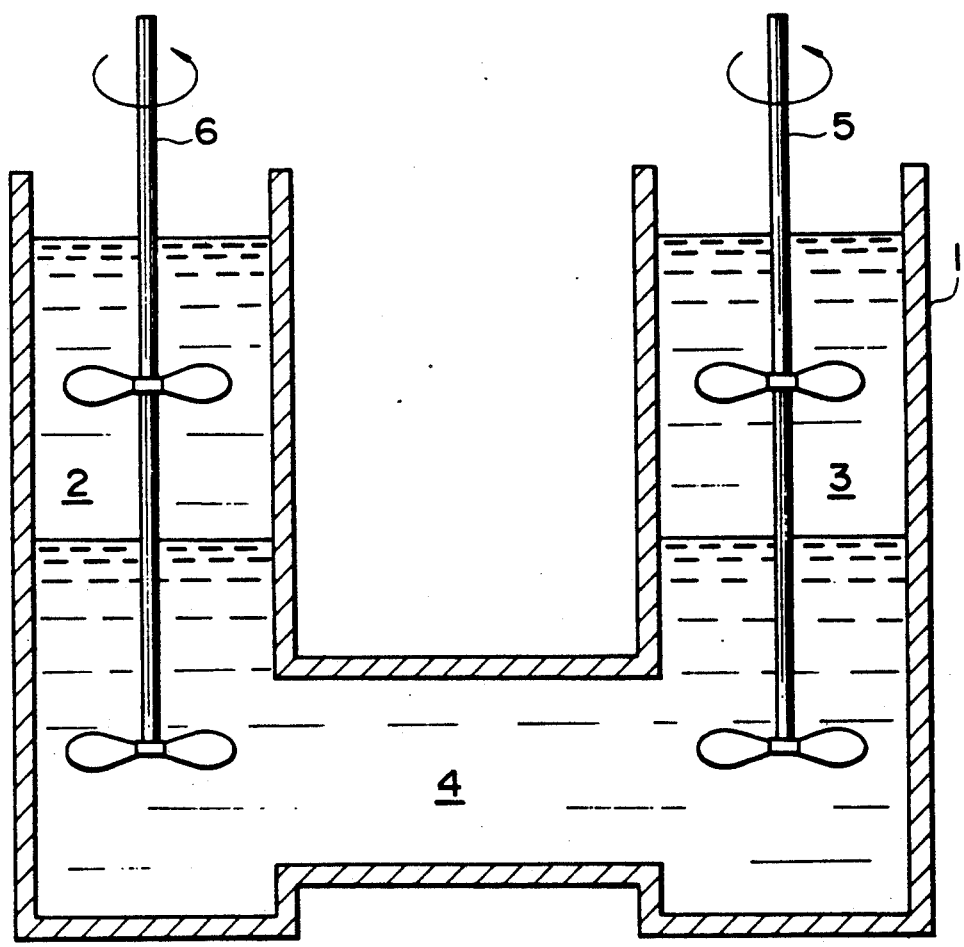

α-AMINO ACID DIAMIDE AND USE THEREOF AS CUPRIC ION-TRANSPORTING IONOPHORE

BACKGROUND OF THE INVENTION

This invention relates to a novel diamide derivative of an α-amino acid. The present invention is also directed to a method for selectively transporting cupric ions contained in a first liquid to a second liquid using the above diamide.

Separation of cupric ions from other heavy metal ions is a very important technique utilized for the recovery and concentration thereof. There are a lot of known extractants and ion transporting agents (ionophores) used for the separation of specific metal ions. An ionophore to be utilized for continuously transporting specific ions contained in a first liquid to a second liquid is required to selectively capture cupric ions. In addition, it is important that the ionophore should release the captured ions to the second liquid in order to effectively perform the continuous transportation of the ions. Known extractants and ionophores, however, are not satisfactory for cupric ions with respect to selectivity or efficiency.

SUMMARY OF THE INVENTION

It is, therefore, the prime object of the present invention to provide a novel diamide derivative of an α-amino acid, which is useful as an ionophore and capable of continuously transporting cupric ions contained in a liquid to another liquid.

Another object of the present invention is to provide a diamide of the above-mentioned type which can transport cupric ions contained in a first liquid to a second liquid even when the concentration of the cupric ions in the first liquid is lower than that in the second liquid.

It is a further object of the present invention to provide a method for transporting cupric ions from a liquid to another liquid.

In accomplishing the foregoing objects, there is provided in accordance with the present invention a diamide expressed by the following general formula (I):

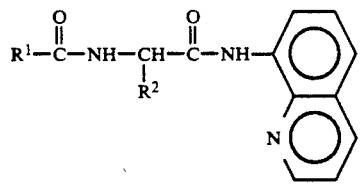

wherein $R^1$ and $R^2$ stand, independently from each other, for a hydrogen atom, an alkyl group, an aralkyl group or an aryl group.

The alkyl group represented by the symbol $R^1$ or $R^2$ is preferably a lower alkyl group having 2-8 carbon atoms. The aralkyl group represented by $R^1$ or $R^2$ is preferably a benzyl group, a phenylethyl group or a phenylpropyl group.

In another aspect, the present invention provides a method of transporting cupric ions in a first liquid to a second liquid, including a step of contacting a third liquid substantially immiscible with the first and second liquids and containing above diamide derivative with the first liquid so that cupric ions in the first liquid are captured by the diamide derivative, and a step of contacting the third liquid containing the cupric ions captured by the diamide derivative with the second liquid so that the cupric ions captured by the diamide derivative are released to the second liquid.

BRIEF DESCRIPTION OF THE DRAWINGS

Other objects, features and advantages of the present invention will become apparent from the detailed description of the invention to follow when considered in light of the accompanying drawing, in which the sole FIGURE is an elevational, cross-sectional view diagrammatically showing an apparatus useful for performing the cupric ion transportation using the diamide derivative of the present invention.

DETAILED DESCRIPTION OF THE INVENTION

The diamide derivative according to the present invention may be obtained in a manner known per se. For example, an —amino acid of the formula (II):

wherein $R^2$ has the same meaning as above, is reacted with an acid anhydride $R^1COOCOR^1$ or an acid chloride $R^1COCl$ to obtain an amide of the formula (III):

wherein $R^1$ has the same meaning as above. The amide of the formula (III) is then reacted with an acid halide of the formula RCOCl, such as pivalyl chloride, to form an acid anhydride of the formula (IV):

wherein R is an alkyl. Subsequently, the acid anhydride of the formula (IV) is reacted with stoichiometric amount of 8-aminoquinoline to obtain the diamide of the formula (I).

The reaction of the acid anhydride (IV) with 8-aminoquinoline may be carried out at a temperature of 0°–120° C., preferably 0°–30° C., using an inert solvent such as benzene, cyclohexane, chloroform, dioxane or tetrahydrofuran.

The diamide derivative according to the present invention, when subjected to a neutral or a weakly acidic condition, i.e. a pH region of about 3-7, can capture cupric ions with a high selectivity. In an acidic condition of a pH range of about below 3, the diamide derivative can liberate the captured cupric ions. Thus, the diamide derivative of the present invention can serve to act as an ionophore or carrier for transporting cupric ions.

The transportation of cupric ions can be done by contacting a first, cupric ion-containing liquid, generally an aqueous liquid having a pH of about 3-7, preferably 5-7, with a third liquid, generally an organic solvent solution, containing the diamide derivative of the present invention and substantially immiscible with the first liquid so that the cupric ions may be captured by the diamide derivative. Illustrative of suitable organic solvents are halogenated organic solvents such as chloroform, carbon tetrachloride and dichloroethane; hydrocarbons such as benzene, toluene and xylene; and alcohols such as octanol and hexanol. The concentration of the diamide in the third liquid is generally in the range of $10^{-5}$ to 1.0 mol/liter, preferably $10^{-3}$ to $10^{-1}$ mol/liter.

The third liquid thus containing the cupric ions captured by the diamide derivative is then contacted with a second liquid, generally an aqueous acidic liquid having a pH of 3 or less, preferably 1-2, and substantially immiscible with the third liquid so that the captured cupric ions are liberated to the second liquid. The second liquid which is to receive cupric ions may be an aqueous liquid containing an inorganic acid such as hydrochloric acid, sulfuric acid or phosphoric acid or an organic acid such as formic acid, acetic acid or an organic sulfonic acid.

One example of cupric ion transportation method will now be described with reference to the accompanying drawing. Referring to the FIGURE, designated by the reference numeral 1 is a U-shaped vessel equipped with stirrer means 5 and 6 in the respective vertical portions thereof. A third, diamide-containing liquid is contained in the vessel 1 to form a third layer 4 with its liquid level positioned adjacent to the respective lower portions of the vertical portions. A first, cupric ion-containing liquid and a second, acidic liquid are poured into the vessel 1 to form first and second layers 2 and 3, respectively, on the third layer 4.

In the interface at which the first and third layers 2 and 4 are contacted, cupric ions in the layer 2 are captured by the diamide contained in the layer 4, while in the interface at which the second and third layers 3 and 4 are contacted, the cupric ions captured by the diamide are liberated and released to the second layer 3. The stirrer means 5 and 6 are continuously operated to facilitate the capture and the liberation of cupric ions. In this method, the third layer 4 should, of course, have a higher specific gravity than the other layers 2 and 3.

If desired, a suitable membrane may be disposed between the first and third liquids and between the second and third liquid. In a special case, the diamide derivative may be supported on a suitable support means such as a filter paper or a high molecular weight membrane and each side of the diamidesupporting means is contacted with respective one of the first and second liquids. The transportation may also be effected by a usual extraction method in which the first and the third liquids are vigorously shaken together to extract the cupric ions with the third liquid, the cupric ions contained in the third liquid being subsequently extracted with the second liquid.

With the diamide derivative according to the present invention, the transportation of cupric ions may be effected continuously at a very high rate. Further, even when the concentration of cupric ions in the first liquid is lower than that of the second liquid, the diamide derivative of this invention can carry cupric ions from the first to the second liquids.

The following examples will further illustrate the present invention.

EXAMPLE 1

Preparation of 8-(N-Acetylphenylalanylamino)quinoline:

In 15 ml of water 8.26 g (50 mmol) of phenylalanine were dissolved. While vigorously stirring this aqueous solution, 10.2 g (100 mmol) of acetic anhydride were added thereto. After the exothermic reaction had been completed, the reaction mixture was further stirred for about 30 minutes and allowed to stand in a refrigerator for about 24 hours. The precipitates thus formed were filtered, washed with water and dried to obtain 7.4 g (yield: 71 %) of N-acetyl-phenylalanine. Then, 1.18 g (5.7 mmol) of this N-acetylphenyl-alanine were dissolved in a solution of 580 mg (5.7 mmol) of triethylamine dissolved in 30 ml of anhydrous tetrahydrofuran. While cooling the resulting solution in an ice bath, 690 mg (5.7 mmol) of pivalyl chloride were added thereto and the mixture was stirred for about 2 hours. To the resulting mixture was added a solution of 820 mg (5.7 mmol) of 8-aminoquinoline dissolved in 10 ml of tetrahydrofuran and the mixture was stirred for about 24 hours. After being added with chloroform, the resulting mixture was washed with a saturated sodium bisulfate solution and then with water, and dried over anhydrous sodium sulfate, followed by distillation in vacuo for the removal of the solvent. The residue was then subjected to column chromatography to obtain 890 mg of a product with a yield of 47%. The NMR, IR and MS spectra reveal that this product is 8-(N-acetylphenylalanylamino)quinoline of the formula (I) in which $R^1$ is metyl and $R^2$ is benzyl. The mass analysis shows:

Calculated: 333.1476 ($C_{20}H_{19}N_3O_2$),
Measured 333.1482.

EXAMPLE 2

Preparation of 8-(N-Acetylalanylamino)quinoline

Example 1 was repeated in the same manner as described except that 8.9 g (10 mmol) of alanine were used in place of 8.26 g of phenylalanine. 8-(N-Acetylalanylamino)quinoline of the formula (I) in which $R^1$ and $R^2$ are each methyl was obtained in an amount of 690 mg (yield: 27%). The mass analysis:

Calculated: 257.1163 ($C_{14}H_{15}N_3O_2$).
Measured: 257.1159.

EXAMPLE 3

Preparation of 8-(N-Formylphenylalanylamino)quinoline

Example 1 was repeated in the same manner as described except that a mixture of 4.6 g (100 mmol) of formic acid and 10.2 g (100 mmol) of acetic anhydride was substituted for 10.2 g of acetic anhydride. 8-(N-Formylphenylalanylamino)quinoline of the formula (I) in which $R^1$ is hydrogen and $R^2$ is benzyl was obtained in an amount of 800 mg (yield: 43%). The mass analysis:

Calculated: 319.1320 ($C_{19}H_{17}N_3O_2$).
Measured: 319.1320.

EXAMPLE 4

Selective Transportation of $Cu^{++}$

The following first, second and third solutions were prepared:

First Solution: 15 ml of an aqueous solution (pH: 6.2) containing 10 mmol/liter of $Cu(OCOCH_3)_2$, 10 mmol/liter of $Ni(OCOCH_3)_2$, 10 mmol/liter of $Co(OCOCH_3)_2$ and 10 mmol/liter of $Zn(OCOCH_3)_2$;

Second Solution: 15 ml of an aqueous 0.1 N sulfuric acid; and

Third Solution: A solution obtained by dissolving $3 \times 10^{-4}$ mol of the compound obtained in Example 1 in 30 ml of chloroform.

These solutions were charged in an apparatus as shown in the FIGURE and the each of the solutions was stirred at 25° C. for two days. Atomic absorption analysis of the resulting second solution revealed that 149 μmol of cupric ions were transported thereto. Substantially no nickel, cobalt or zinc ions were detected.

EXAMPLE 5

Rate of Transportation of Cu++

Example 4 was repeated in the same manner as described except that 15 ml of an aqueous solution (pH: 6.2) containing 10 mmol/liter of Cu(OCOCH$_3$)$_2$ was used as the first liquid and that the stirring was continued for 3 days. The amount of cupric ions in the second liquid was measured after 0.5, 1 and 2 days from the commencement of the test. The results were as summarized in Table 1. In Table 1, the transportation rate (R) is calculated according to the following equation:

$$R = \frac{\text{Amount of cupric ions in 2nd soln.} \times 100 \, (\%)}{\text{Amount of cupric ions originally present in 1st soln.}}$$

TABLE 1

| Process Time (day) | 0.5 day | 1 day | 2 days |
| --- | --- | --- | --- |
| Amount of Cu++ (μmol) | 86 | 123 | 147 |
| Transportation Rate R (%) | 59 | 82 | 98 |

COMPARATIVE EXAMPLES 1-4

Example 5 was repeated in the same manner as described except that $3 \times 10^{-4}$ mol of the diamide compound obtained in Example 1 was replaced by $3 \times 10^{-4}$ mol of 2,2-dibutyl-N,N'-bis(8-quinolyl)maronamide (Comparative Example 1), $3 \times 10^{-4}$ mol of N,N'-bis(8-quinolyl)succinamide (Comparative Example 2), $6 \times 10^{-4}$ mol of Kelex 100 (Comparative Example 3) or $3 \times 10^{-4}$ mol of N,N'-bis(8-quinolyl)glutaramide (Comparative Example 4) and that the stirring was continued for 2 days. The amount of cupric ions transported to the second liquid after 2 days is shown in Table 2 together with the result of Example 5.

TABLE 2

| | Amount of Cu++ (μmol) |
| --- | --- |
| Example 5 | 147 |
| Comparative Example 1 | 3 |
| Comparative Example 2 | 23 |
| Comparative Example 3 | 50 |
| Comparative Example 4 | 95 |

EXAMPLES 6

Example 4 was repeated in the same manner as described except that 15 ml of an aqueous solution (pH: 6.2) containing 10 mmol/liter of Ni(OCOCH$_3$)$_2$ was used as the first liquid. No 5 nickel ions were detected in the second solution after 2 days stirring.

EXAMPLE 7

Rate of Transportation of Cu++

Example 4 was repeated in the same manner as described except that a solution obtained by dissolving $3 \times 10^{-4}$ mol of the compound obtained in Example 3 in 30 ml of chloroform was used as the third liquid. The amount of cupric ions in the second liquid was measured after 0.5, 1 and 2 days from the commencement of the test. The results were as summarized in Table 3.

TABLE 3

| Process Time (day) | 0.5 day | 1 day | 2 days |
| --- | --- | --- | --- |
| Amount of Cu++ (μmol) | 75 | 105 | 128 |
| Transportation Rate R (%) | 80 | 131 | 146 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A diamide expressed by the following general formula (I):

$$R^1-\overset{O}{\underset{}{C}}-NH-\underset{R^2}{\overset{}{CH}}-\overset{O}{\underset{}{C}}-NH-\text{(8-quinolyl)} \quad (I)$$

wherein R$^1$ and R$^2$ stand, independently from each other, for a hydrogen atom, an alkyl group, an aralkyl group or an aryl group.

2. A diamide derivative as claimed in claim 1, wherein said alkyl group is a lower alkyl group having 2-8 carbon atoms.

3. A diamide derivative as claimed in claim 1, wherein said aralkyl group is selected from the group consisting of a benzyl group, a phenylethyl group and a phenylpropyl group.

4. 8-(N-Acetylphenylalanylamino)quinoline.
5. 8-(N-Acetylalanylamino)quinoline.
6. 8-(N-Formylphenylalanylamino)quinoline.

* * * * *

UNITED STATES PATENT AND TRADEMARK OFFICE
CERTIFICATE OF CORRECTION

PATENT NO. : 5,182,398

DATED : January 26, 1993

INVENTOR(S) : KASUGA et al

It is certified that error appears in the above-identified patent and that said Letters Patent is hereby corrected as shown below:

Col. 4, line 46, delete "$N_{3O2}$" and insert --$N_3O_2$--.

Signed and Sealed this

Fourth Day of January, 1994

*Attest:*

BRUCE LEHMAN

*Attesting Officer*    *Commissioner of Patents and Trademarks*